(12) United States Patent
Whiley et al.

(10) Patent No.: US 7,998,668 B2
(45) Date of Patent: Aug. 16, 2011

(54) NEISSERIA GONORRHOEAE DETECTION

(75) Inventors: David Mark Whiley, Brighton (AU);
Theo Pieter Sloots, River Hills (AU)

(73) Assignee: The State of Queensland Acting Through Its Department of Health, Queensland (AU)

( * ) Notice: Subject to any disclaimer, the term of this patent is extended or adjusted under 35 U.S.C. 154(b) by 1315 days.

(21) Appl. No.: 10/599,699

(22) PCT Filed: Apr. 6, 2005

(86) PCT No.: PCT/AU2005/000500
§ 371 (c)(1),
(2), (4) Date: Oct. 30, 2006

(87) PCT Pub. No.: WO2005/098028
PCT Pub. Date: Oct. 20, 2005

(65) Prior Publication Data
US 2009/0130656 A1    May 21, 2009

(30) Foreign Application Priority Data

Apr. 8, 2004   (AU) ............................... 2004901890

(51) Int. Cl.
*C12Q 1/68* (2006.01)
*C07H 21/04* (2006.01)
*C40B 40/06* (2006.01)

(52) U.S. Cl. ........ 435/6; 536/23.1; 536/24.3; 536/24.33

(58) Field of Classification Search .................. None
See application file for complete search history.

(56) References Cited

OTHER PUBLICATIONS

Glustein et al., Molecular Diagnosis 4(3): 233-239 (1999).
McKnew et al., Journal of Infectious Diseases 187: 1213-1222 (2003).
Tabrizi et al., Sexually Transmitted Infections 80: 68-71 (2004).
Whiley el al., European Journal of Clinical Microbial Infectious Diseases 23: 705-710 (2004).

*Primary Examiner* — Robert A Zeman
(74) *Attorney, Agent, or Firm* — Perkins Coie LLP

(57) ABSTRACT

A method for determining whether a human individual is or has been infected with *Neisseria gonorrhoeae*, is provided. The method detects a *Neisseria gonorrhoeae*, porA nucleic acid fragment obtained from a biological sample. The method includes subjecting the biological sample to nucleic acid sequence amplification using primers having respective nucleotide sequences according to SEQ ID NO:1 and SEQ ID NO:2, to thereby produce a porA *Neisseria gonorrhoeae*, amplification product. The amplification product is detected by fluorescence resonance energy transfer using oligonucleotides having respective nucleotide sequences according to SEQ ID NO:3 which has a donor fluorophore and SEQ ID NO:4, which has an acceptor fluorophore.

12 Claims, 1 Drawing Sheet

NGpapLC oligonucleotides:

NG-pap-1:  CGGTTTCCGTGCGTTACGA       cggtttccgtgcgttacga
NG-pap-2:  CTGGTTTCATCTGATTACTTTCCA  tggaaagtaatcagatgaaaccag (AS))

NG-pap-p1: CATTCAATTTGTTCCGAGTCAAAACAGC  cattcaatttgttccgagtcaaaacagc
NG-pap-p2: AGTCCGCCTATACGCCTGCTACTTTCAC  agtccgcctatacgcctgctactttcac

Additional oligos

NG-pap-3:  TGCTACTTTCACGCTGGAAAGTA       tgctactttcacgctggaaagta
NG-pap-4:  GAAAGTAATCAGATGAAACCAGTTC     gaaagtaatcagatgaaaccagttc
NG-pap-5:  AGGGGCATGATGCTTTCTTTTTGTTC    aggggcatgatgctttcttttgttc
NG-pap-6:  CTTGCTCGGCAGAGCGAGTGATA       cttgctcggcagagcgagtgata
NG-pap-7:  GCCGAGCAAGAACAAAAGAAAGCA      tgctttcttttgttcttgctcggc (AS))

Aaggtctgtatttaaatcatgttgcgggaaagcaacattttcaaaaaagttaatttattgttttatatt
gaaatattattttcaaaataaaaatcccaaaattttacccgaaatttgttccgaaaaatggttttttttt
cggggggggtaattggagactgattgggtgtttgcccgatgtttttagcaaatttacaaaaggaagccg
atatgcgaaaaaaacttaccgccctcgtattgtccgcactgccgtttgcggcagttgccgatgtcggcc
tgtacggcgaagtcaaagctggtgtggaaggcaggaacatccggctgcagttgaccgagccacctcag
aaggtcaaacgggcaatacagttactaaggccaaaagccgcatcaggacgaaagtcagtgatttcggct
cgtttatcggctttaaggggtgggatttgggcggcgggctgaaggctgtttggcagctcgagcaaga
cgtatccgttgccggcggcgcgaccegttggggtaacagggaatcctttatcggcttggcaggcga
attcggcacggcgctcgccggtcgcgttgcgaatccgtttggcgatgccagcaaagccattgatccttg
ggacagcaataataatgtggcttcgcaattgggtattttcaaacgccacgacggtatgc ...cggtttccgtgcgttacgattccccggattttccggtttcagcggcagcattcaatttgttccga
gtcaaaacagcaagtccgcctatacgcctgctactttcacctggaaagtaatcagatgaaaccagttc
cggctgttgtcggcaagccgggtcggatgtgtattatgccggtctgaattacaaaaatggcggggttt
tcggaaattatgccgttaaatatgcgaaacacgccaatgaggggcatgatgctttcttttgttcttgc
tcggcagagcgagtgatac...

cgatccattgaaaaaccatcaggtacaccgcctgacgggcggctatgaggaagcggcttgaatctcgcc
ttggcggctcagttggatttgtctgaaaatgccgacaaaaccaaaaacagtacgaccgaaattgccgcc
actgcttcctaccgcttcggtaatacagtccgcgcatcagctatgcccatggtttcgactttgtcgaa
cgcagtcagaaacgcgaacataccagctatgatcaaatcatcgccggtgtcgattacgatttttccaag
cgcacttccgccatcatgtctgccgcttggctgaaacgaaataccggcatcggcaactacactcaaatt
aatgccgcctccgttggtctgcgccacaaattc

*FIG.1*

NEISSERIA GONORRHOEAE DETECTION

This application is a national stage of PCT/AU2005/000500 filed Apr. 6, 2005, the entirety of which is hereby incorporated by reference.

FIELD OF THE INVENTION

THIS INVENTION relates to detection of the bacterium *Neisseria gonorrhoeae*, more particularly to detection of bacterial nucleic acids. This invention particularly relates to the detection of amplified fragments of a porA gene of *Neisseria gonorrhoeae*, for determining, whether the bacterium is present in a biological sample obtained from an individual, typically for the proposes of clinical diagnosis.

BACKGROUND OF THE INVENTION

*Neisseria gonorrhoeae*, is a gram-negative diplococcal bacterial pathogen which is the causative organism of the sexually transmitted disease (STD) known as gonorrhoea. Although gonorrhoea is an ancient disease first described by Galen in AD 150, it is still a major STD of humans. Failure to detect and treat *Neisseria gonorrhoeae* infection can allow the disease to progress to a serious systemic infection that affects the heart, joints, meninges, eyes and pharynx. Thus, early definitive diagnosis can assist treatment of the disease and prevent the serious complications that can arise as a result of this bacterial infection.

Although polymerase chain reaction (PCR) is the method of choice for routine detection of *Neisseria gonorrhoeae*, PCR has limitations and bacterial isolation has remained the gold standard for definitive diagnosis. This is largely because *N. gonorrhoeae* shares much sequence homology with other *Neisseria* species, including *N. meningitidis*, and in addition, contains many non-conserved sequences (Palmer et al., 2003, J. Clin. Microbiol. 41 835-7). Thus, there is a potential for both false-positive and false-negative results to occur when using PCR for routine detection of *N. gonorrhoeae*. In both situations the consequences may be significant. From a public health perspective, false-negative results may allow unchecked spread of the disease whereas false-positive results can have considerable social ramifications for patients.

The Roche Cobas Amplicor system (Roche Diagnostics, Australia) is a PCR assay widely used for the detection of *N. gonorrhoeae*. Its appeal lies in its ability to simultaneously detect *N. gonorrhoeae, Chlamydia trachomatis* and the presence of inhibiting substances, while also carrying United States Food and Drug Administration (FDA) approval. However, the Cobas Amplicor system does have limitations. Most, notably, its *N. gonorrhoeae* assay is known to cross react with some strains of commensal *Neisseria* species, including *N. subflava, N. cinerea, N. flavescens, N. lactamica* and *N. sicca* (Palmer et al., 2003, supra; Farrell, 1999, J. Clin. Microbiol. 37 386-90). Consequently, there is a need to use a second PCR assay to confirm Cobas Amplicor positive results. In response, clinical laboratories have adopted in-house confirmatory assays.

To date, the most common target for in-house confirmatory tests has been the cryptic plasmid (cppB) gene of *N. gonorrhoeae*, with several such protocols having been described (Ho et al., 1992, J. Clin Pathol. 45 439-442; Farrell, 19995 supra; Whiley et al., 2002, Diagn. Microbiol. Infect. Dis. 42 85-9; Tabrizi et al., 2004, Sex. Trans. Infect 80 68-71). In particular, a LightCycler based cppB PCR (cppB-LC) assay has been developed for conformation of Cobas *N. gonorrhoeae* positive specimens (Whiley et al., 2002, supra). However, serious concerns have now been raised over the sensitivity and specificity of *N. gonorrhoeae* assays targeting the cppB gene. Studies conducted in both the United Kingdom and Australia have identified *N. gonorrhoeae* isolates lacking the cppB gene (Palmer et al. 2003, supra, Ottawa; A cluster of culture-positive, but PCR false negative infections with *Neisseria gonorrhoeae*. Tapsall et al., Abstract 0129. 15th Biennial Congress of the International Society for Sexually Transmitted Diseases Research ISSTDR). Therefore, laboratories targeting this gene run the risk of false-negative results. In addition, the cppB gene could be present in commensal *Neisseria* strains, including *N. cinerea*, and so could also produce false-positive results (Palmer et al. 2003, supra).

Cross-reaction is a significant problem for gonococcal nucleic acid-based diagnostic testing and horizontal genetic exchange in the *Neisseria* genus is the major source of these cross-reactions (Johnson et al., 2002, MMWR Recomm. Rep 18 1-38). Furthermore, gonococcal tests are used on non-sterile sites and other *Neisseria* strains may frequently be found in such sites.

PCR detection of the porA gene has been used to detect. *Neisseria meningitidis* (Glustein et al., 1999, Molecular Diagnosis 4 233-9), partly due to an assumption that is gene is absent in commensal *Neisseria* (Feavers & Maiden, 1998, Mol. Microbiol. 30 647-656). Furthermore, in such assays, cross-reaction (or the potential for cross-reaction) is not a significant threat as these tests are used on sterile sites, including blood and CSF.

The only other *Neisseria* species where a porA sequence has been identified is *N. gonorrhoeae*, which has a porA pseudogene of considerable sequence similarity to the *N. meningitidis* porA gene (Feavers & Maiden, 1998, supra). However, it is not clear whether this pseudogene is present in all strains of *N. gonorrhoeae*, nor has its absence in commensal strains been verified.

SUMMARY OF THE INVENTION

Notwithstanding the fact that the *N. gonorrhoeae* porA pseudogene is an unlikely target for nucleic acid-based detection of *N. gonorrhoeae* and, more particularly for distinguishing between *N. gonorrhoeae* and *N. meningitidis*, and might not be present ubiquitously among *N. gonorrhoeae* isolates and strains or absent in commensal strains, the present inventors have developed a surprisingly sensitive and reproducible nucleic acid-based detection method using the *N. gonorrhoeae* porA pseudogene as a target.

The present invention is therefore broadly directed to an method of determining whether an individual is or has been infected with *Neisseria gonorrhoeae*, which method utilizes a porA pseudogene or porA nucleic acid derived therefrom, as an indicator of infection.

The present, invention is also broadly directed to one or more oligonucleotides which facilitate detection of a *Neisseria gonorrhoeae*, porA gene or porA nucleic acid.

In a first aspect the invention provides a method of determining whether an individual is or has been infected with *Neisseria gonorrhoeae*, said method including the step of detecting an isolated porA nucleic acid of *Neisseria gonorrhoeae*, if present in a biological sample obtained from said individual, a presence of said porA nucleic acid indicating that said individual is or has been infected with *Neisseria gonorrhoeae*.

Preferably, the method includes the step of subjecting a nucleic acid sample to nucleic acid sequence amplification under conditions which facilitate amplification of said isolated porA nucleic acid to a detectable level.

In a second aspect the invention provides a method of determining whether an individual is or has been infected with *Neisseria gonorrhoeae*, said method including the step of selectively detecting or distinguishing an isolated porA nucleic acid of *Neisseria gonorrhoeae*, from a porA nucleic of another *Neisseria* species if present in said biological sample obtained from said individual, a presence of said isolated porA nucleic acid indicating mat said individual is or has been infected with *Neisseria gonorrhoeae*.

Preferably, the method includes the step of subjecting a nucleic acid sample to nucleic acid sequence amplification under conditions which facilitate amplification of said isolated porA nucleic acid to a detectable level but which do not facilitate amplification of said porA nucleic of said another *Neisseria* species to a detectable level.

Preferably, said another *Neisseria* species is *N. meningitidis*.

In a preferred embodiment the invention provides a method of determining whether a human individual is or has been infected with *Neisseria gonorrhoeae* said method inducing the steps of:

(i) subjecting a biological sample obtained from said human individual to nucleic acid sequence amplification to selectively produce a porA *Neisseria gonorrhoeae*, amplification product from a *Neisseria gonorrhoeae*, porA nucleic acid if present in said biological sample; and (ii) detecting said amplification product, if present, by probe hybridization whereby a presence of said porA amplification product indicates that said individual is or has been infected with *Neisseria gonorrhoeae*.

In a third aspect, the invention provides an oligonucleotide which is capable of hybridizing to a porA nucleic acid of *Neisseria gonorrhoeae*, sufficiently to enable detection of said porA nucleic acid, but which is not capable of hybridizing to a porA nucleic acid of another *Neisseria* species sufficiently to enable detection of said porA nucleic acid of said another *Neisseria* species.

Preferably, said another *Neisseria* species is *N. meningitidis*.

In preferred embodiments, said oligonucleotide comprises a nucleotide sequence as set forth in Table 1 and FIG. 1 (SEQ ID NOS:3-9).

In a fourth, aspect, the invention provides a kit comprising one or more oligonucleotides according to the third aspect together with a DMA polymerase and/or one or more detection reagents.

In a fifth aspect the invention provides a nucleic acid array comprising an oligonucleotide according to the second aspect, immobilized, coupled, impregnated or otherwise in communication with a substrate.

It will be appreciated that the invention provides a method and oligonucleotide mat facilitate detection of a porA nucleic acid of *Neisseria gonorrhoeae*.

Preferably the porA nucleic acid corresponds to a fragment of a porA pseudogene of *Neisseria gonorrhoeae*.

More preferably, according to tins embodiment the porA nucleic acid corresponds to a fragment of a porA pseudogene of *Neisseria gonorrhoeae*, which fragment has a nucleotide sequence distinct from a fragment of a porA gene or pseudogene of another *Neisseria* species.

In a particularly preferred embodiment, the porA nucleic acid of *Neisseria gonorrhoeae*, comprises a nucleotide sequence to which an oligonucleotide is capable of annealing sufficient to enable detection of said porA nucleic acid.

Suitably, said nucleotide sequence is not present in, or has one or more nucleotides different to, a nucleotide sequence of a porA nucleic acid of another *Neisseria* species, such that said oligonucleotide is not capable of hybridizing to said porA nucleic acid of said another *Neisseria* species sufficient to facilitate detection of said porA nucleic acid of said another *Neisseria* species.

Preferably, said another *Neisseria* species is *N. meningitidis*.

In a particularly advantageous embodiment, the method and oligonucleotide of the invention facilitate detection of a porA nucleic acid feat may be present in each, of a plurality of isolates, strains, allelic variants or sub-species of *Neisseria gonorrhoeae*.

Throughout tins specification, unless otherwise indicated, "comprise", "comprises" and "comprising" are used inclusively rather than exclusively, so that a stated integer or group of integers may include one or more other non-stated integers or groups of integers.

BRIEF DESCRIPTION OP THE FIGURES

FIG. 1 List of preferred oligonucleotide primer sequences (AS=antisense) and nucleotide sequence of *N. gonorrhoeae* porA pseudogene. Bolded residues indicate (5' to 3') NG-pap-F (forward) primer annealing site; NG-pap-p1 probe hybridization site; NG-pap-p2 probe hybridization site; and NG-pap-R (reverse) primer annealing site. The expected amplification product size is 132 bp. Shaded residues are those which are non-identical with the corresponding *N. meningitides* porA sequence: (SEQ ID NO:1); NG-pap-R (reverse) primer sequence (SEQ ID NO:2/SEQ ID NO: 11); NG-pap-p1 probe (SEQ ID NO: 3); NG-pap-p2 probe sequence (SEQ ID NO: 4); NG-pap-p3 probe sequence (SEQ ID NO: 5); NG-pap-p4 probe sequence (SEQ ID NO: 6); NG-pap-p5 probe sequence (SEQ ID NO: 7); NG-pap-p6 probe sequence (SEQ ID NO: 8); NG-pap-p7 probe sequence (SEQ ID NO: 9/SEQ ID NO: 12); *N. gonorrhoeae* porA pseudogene sequence (SEQ ID NO:10/SEQ ID NO: 13/SEQ ID NO: 14);

DETAILED DESCRIPTION OF THE PREFERRED EMBODIMENT

The present invention is directed to improving nucleic acid-based detection of *N. gonorrhoeae*. To this end the present inventors have identified an alternative PCR target sequence on the *N. gonorrhoeae* genome, namely the porA pseudogene, which has never before been used as a target for *N. gonorrhoeae* detection and unexpectedly offers drastically improved clinical, sensitivity and specificity for the detection of *N. gonorrhoeae* when compared with other PCR assays described to date.

More particularly, the present inventors have developed a new *N. gonorrhoeae* LightCycler™ assay targeting the *N. gonorrhoeae* porA pseudogene. Importantly, the *Neisseria* porA gene is shown to be present in all *N. gonorrhoeae* samples and isolates tested bat absent in commensal *Neisseria* species. Therefore, the selection of this gene target eliminates or at least reduces the potential for cross-reaction with commensal *Neisseria* species.

Differences existing in porA sequences between *N. gonorrhoeae* and *N. meningitidis* have also been exploited to develop oligonucleotides that enable specific PCR amplification and detection of *N. gonorrhoeae*-derived porA nucleic acids only.

A particular difficulty overcome by the present invention is that there are only a few, small sections of porA sequence with sufficient difference between *N. gonorrhoeae* and *N. meningitidis* to develop a specific gonococcal assay. Too few mismatches between amplification primers and contaminating DNA, namely meningococcal porA DNA, will cause the assay to cross-react. Too many mismatches between primers and their respective targets may decrease the amplification efficiency of PCR amplification of the gonococcal target porA sequence.

The oligonucleotide primers of the invention have sufficient mismatches so as to make the assay specific for gonococcal porA DNA, even when contaminated with relatively high concentrations of meningococcal DNA (approximately 0.5 μg per reaction).

The present invention therefore provides a method for detecting an isolated porA nucleic acid of *Neisseria gonorrhoeae*, in a biological sample and one or more oligonucleotides, which facilitate amplification and/or detection of said porA nucleic acid.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical synthetic or recombinant form.

As used herein, "nucleic acid" includes and encompasses DNA, RNA and PNA-RNA hybrids. DNA includes single-stranded and double-stranded genomic DNA and cDNA as are well understood in the art. RNA includes single-stranded and double-stranded unprocessed RNA, mRNA and tRNA.

It will be appreciated that by "porA nucleic acid" is meant a nucleic acid which corresponds to at least a fragment or region of a porA gene or pseudogene.

As used herein, a "gene" is a discrete structural unit of a genome which may comprise one or more elements such as an amino acid coding region typically present in one or more cistrons, an operator, a promoter, a terminator and/or any other regulatory nucleotide sequence(s).

As used herein a "pseudogene" is an inactive unit, region or sequence of a genome which has a similar sequence to a known functional gene. Typically, because of this sequence similarity, pseudogenes are normally considered to be evolutionary relatives to normally functioning; genes.

In *N. gonorrhoeae*, porA is a pseudogene while in *N. meningitidis* porA is a gene.

By "corresponds to" or "corresponding to" in tins context in meant that the porA nucleic acid comprises a nucleotide sequence which is present in an porA pseudogene, or is complementary to a nucleotide sequence present in a porA pseudogene, or is at least 80%, preferably at least 85%, more preferably at least 90% or even more preferably at least 95%, 96%, 97%, 98% or 99% identical to either of these.

In a particularly preferred embodiment the porA nucleic acid corresponds to a 132 bp fragment of a porA pseudogene.

In particular aspects, the invention provides one or more oligonucleotides and/or methods of using same for facilitating nucleic acid sequence amplification and/or detection of a porA nucleic acid.

As used herein, an "oligonucleotide" is a single- or double-stranded nucleic acid having no more than one hundred (100) nucleotides (bases) or nucleotide pairs (base pairs). A "polynucleotide"1 has more than one hundred (100) nucleotides or nucleotide pairs.

In the particular context of nucleic acid sequence amplification, an oligonucleotide of the invention may be in the form of a primer.

As used herein, a "primer" is a single-stranded oligonucleotide which is capable of hybridizing to a nucleic acid "template" and being extended in a template-dependent fashion by the action of a suitable DNA polymerase such as Taq polymerase, RNA-dependent DNA polymerase or Sequenase™.

Typically, a primer may have at least twelve, fifteen, twenty, twenty-five, thirty, thirty five or forty but no more than fifty contiguous nucleotide bases.

It will be appreciated that the primers described herein have been designed according to selected criteria to maximize detection sensitivity and specificity.

Suitably, primers of the invention are designed to be capable of annealing to a nucleotide sequence of a *Neisseria gonorrhoeae*, porA nucleic acid that is not present in, or has one or more nucleotides different to, a nucleotide sequence of a porA nucleic acid of another *Neisseria* species, such that said oligonucleotide is not capable of annealing to said porA nucleic acid of said another *Neisseria* species sufficient to facilitate detection of said porA nucleic acid of said another *Neisseria* species.

Preferably, said another *Neisseria* species is *N. meningitidis*.

It will also be appreciated that the present invention is predicated, in part, on the observation that other, commensal *Neisseria* species such as *N. subflava, N. cinerea, N. flavescens, N. lactamica* and *N. sicca* do not have a porA pseudogene.

In one particularly advantageous embodiment, primers of the invention are designed to facilitate detection of a porA nucleic acid of a plurality of isolates, strains, allelic variants or sub-species of *Neisseria gonorrhoeae*.

Accordingly, the present inventors have identified nucleotide sequences in a porA gene of *Neisseria gonorrhoeae*, which are conserved within a plurality of isolates of this pathogenic organism, which sequences are not present in, or are sufficiently different to, respective nucleotide sequences in a porA pseudogene of *Neisseria meningitidis*.

This has enabled the present inventors to design primers that facilitate specific, sensitive and broad-spectrum amplification of *Neisseria gonorrhoeae*, porA nucleic acids while avoiding amplification of a porA nucleic acid of said another *Neisseria* species, or at least minimizing amplification thereof to an undetectable level.

Particular examples of primers according to the invention are provided in FIG. 1 and Table 1 (SEQ ID NOS: 1 and 2).

It will be appreciated from comparing the primer sequences of FIG. 1 (SEQ ID NOS:1 and 2), the *N. gonorrhoeae*, porA pseudogene nucleotide sequence set forth in FIG. 1 (SEQ ID NO: 10) and the corresponding published *N. meningitidis* porA nucleotide sequence, that variations in primer sequence are readily achievable while maintaining the specificity necessary for selectively amplifying a *N. gonorrhoeae*, porA sequence.

In a preferred embodiment the invention contemplates detection of a porA nucleic acid or fragment thereof by nucleic acid sequence amplification and subsequent detection of a porA amplification product Nucleic acid amplification techniques are well known to the skilled addressee, and include polymerase chain reaction (PCR) and ligase chain reaction (LCR) as for example described in Chapter 15 of Ausubel et al. CURRENT PROTOCOLS IN MOLECULAR BIOLOGY (John Wiley & Sons NY, 1995-1999); strand displacement amplification (SDA) as for example described in U.S. Pat. No. 5,422,252; roiling circle replication (RCR) as for example described in Liu et al., 1996, J. Am. Chem. Soc. 118 1387 and International application WO 92/01813 and by Lizardi et al., in International Application WO 97/19193; nucleic acid sequence-based amplification (NASBA) as for example described by Sooknanan et al., 1994, Biotechniques 17 1077; Q-β replicase amplification as for example described by Tyagi et al., 1996, Proc. Natl. Acad. Sci. USA 93 5395 and helicase-dependent amplification as described in International Publication WO2004/02025.

The abovementioned are examples of nucleic acid sequence amplification techniques but are not presented as an exhaustive list of techniques. Persons skilled in the art will, be well aware of a variety of other applicable techniques as well as variations and modifications to the techniques described herein.

For example, the invention contemplates use of particular techniques that facilitate quantification of nucleic acid sequence amplification products such as by "competitive PCR", or techniques such as "Real-Time" PCR amplification such as described in Whiley et al., 2002, supra.

Preferably, the nucleic acid sequence amplification technique is PCR.

As used herein, an "amplification product" is a nucleic acid generated by a nucleic acid sequence amplification technique as hereinbefore described.

In a particularly preferred embodiment the method produces a single 132 bp porA amplification product.

As used herein, "hybridization", "hybridize" and "hybridizing" refers to formation of a hybrid nucleic acid through base-pairing between complementary or at least partially complementary nucleotide sequences under defined conditions, as is well known in the art. Normal base-pairing occurs through formation of hydrogen bonds between complementary A and T or U bases, and between G and C bases. It will also be appreciated that base-pairing may occur between various derivatives of purines (G and A) and pyrrolidines (C, T and U). Purine derivatives include inosine, methylinosine and methyladenosines. Pyrimidine derivatives include sulfur-containing pyrimidines such as thiouridine and methylated pyrimidines such as methylcytosine. For a detailed discussion of the factors that generally affect nucleic acid hybridization, the skilled addressee is directed to Chapter 2 of CURRENT PROTOCOLS IN MOLECULAR BIOLOGY, supra.

More specifically, the terms "anneal" and "annealing" are used in the context of primer hybridisation to a nucleic acid template for a subsequent primer extension reaction, such as occurs during nucleic acid sequence amplification or dideoxy nucleotide sequencing, for example.

For a discussion of the factors that affect annealing of PCR primers, the skilled addressee is directed to Chapter 15 of CURRENT PROTOCOLS IN MOLECULAR BIOLOGY Eds Ausubel et al. (John Wiley & Sons NY 1995-1999).

The invention provides detection of a porA nucleic acid of *Neisseria gonorrhoeae*, in a biological sample as an indication or the presence of a *Neisseria gonorrhoeae*, in an individual from which the biological sample has been derived or obtained, or as an indication of a past *Neisseria gonorrhoeae*, infection of said individual.

Preferably, a porA nucleic acid amplification product, which amplification product is detected by one or more methods as well understood in the art.

Detection of amplification products may be achieved by detection of a probe hybridized to an amplification product, by direct visualization of amplification products by way of agarose gel electrophoresis, nucleotide sequencing of amplification products or by detection of fluorescently-labeled amplification products.

As used herein, a "probe" is a single- or double-stranded oligonucleotide or polynucleotide, one and/or the other strand of which is capable of hybridizing to another nucleic acid, to thereby form a "hybrid" nucleic acid Probes and/or primers of the invention may be labeled, for example, with biotin or digoxigenin, with fluorochromes or donor fluorophores such as FITC, TRITC, Texas Red, TET, FAM6, HEX, ROX or Oregon Green, acceptor fluorophores such as L-Red640, enzymes such as horseradish peroxidase (HRP) or alkaline phosphatase (AP) or with radionuclides such as $^{125}$I, $^{32}$P, $^{33}$P or $^{35}$S to assist detection of amplification products by techniques are well known in the art.

Preferred embodiments of probes according to the present invention have respective nucleotide sequences set forth, in FIG. 1 and Table 2 (SEQ ID NOS:3-9).

Particularly preferred embodiments of probes according to the present invention have respective nucleotide sequences set forth in SEQ ID NOS: 3 and 4.

With regard to detection of fluorescently-labelled amplification products, this may be achieved using one or more primers that incorporate fluorescent labels as hereinbefore described.

In another embodiment, detection may be performed by melting curve analysis using probes incorporating fluorescent labels that hybridize to amplification products in a sequence amplification reaction. A particular example is the use of Fluorescent Resonance Energy Transfer (FRET) probes to hybridize with amplification products in "real time" as amplification products are produced with each cycle of amplification.

A FRET hybridization probe pair is designed to hybridize to adjacent regions on a target DNA. Each probe is labeled with a different marker dye. Interaction of the two dyes can only occur when both are bound to their target. Typically, the donor probe is labeled with a fluorophore (such as FITC, TRITC, Texas Red, TET, FAM6, HEX, ROX or Oregon Green) at the 3' end and the acceptor probe is labelled with an acceptor fluorophore (such as LC-Red640, TAMRA or QSY dyes) at its 5' end. During PCR, the two different oligonucleotide probes hybridize to adjacent regions of the target DNA such that the fluorophores, which are coupled to the oligonucleotides, are in close proximity in the hybrid structure. The donor fluorophore is excited by an external light source, then passes part of its excitation energy to the adjacent acceptor fluorophore. The excited acceptor fluorophore emits light at a different wavelength which can then be detected and measured.

In yet another embodiment, the invention contemplates use of melting curve analysis whereby nucleic acid-intercalating dyes such as ethidium bromide (EtBr) or SYBR Green I bind amplification products and fluorescence emission by the intercalated complexes is detected.

Melting curve analysis may advantageously be performed using an apparatus such as a LightCycler™, as for example described in Whiley et al., 2002, supra.

In light of the foregoing, it will be apparent that the *Neisseria gonorrhoeae*, detection methods of the invention are ideally suited to assisting diagnosis of individuals that may have had, or currently have, a *Neisseria gonorrhoeae*, infection.

*Neisseria gonorrhoeae*, is a primarily a pathogenic organism of humans, hence the present invention is particularly directed to detection of *Neisseria gonorrhoeae*, infection in human individuals.

Suitably, said biological sample is a cervical, urethral, penile, anal, rectal, throat, saliva, fecal or urine sample, although without limitation thereto.

Suitably, said biological sample includes one or more bacteria or nucleic acid(s) derived therefrom which may be in the form of DNA or RNA.

Preferably, in order to minimize handling of said biological sample, genomic DNA is isolated from said biological sample according to the method of the invention. However, in principle, cDNA could be generated by reverse-transcribing isolated RNA as is well known in the art, as for example described in Chapter 15 of CURRENT PROTOCOLS IN MOLECULAR BIOLOGY, supra.

Particularly for the purpose of clinical diagnosis, although, without limitation thereto, the invention provides a kit comprising one or more oligonucleotides such as a primer pair according to the third aspect of the invention, Said kit may further comprise other reagents such as a thermostable DNA polymerase, a porA nucleic acid probe, positive and/or negative nucleic acid control samples, molecular weight markers, detection reagents such as for colorimetric detection or fluorescence detection of amplification products and/or reaction vessels such as microtitre plates.

It will also be appreciated that the method of the invention may be used alone or combined with other forms of diagnosis, such as bacterial culture tests or traditional diagnosis based on clinical symptoms, to improve the accuracy of diagnosis.

In a preferred embodiment the invention provides a method of determining whether a human individual is or has been infected with *Neisseria gonorrhoeae*, said method including the steps of:

(i) subjecting a biological sample obtained from said human individual to nucleic acid sequence amplification to selectively produce a porA *Neisseria gonorrhoeae*, amplification product from a *Neisseria gonorrhoeae*, porA nucleic acid if present in said biological sample; and (ii) detecting said amplification product, if present, by probe hybridization whereby a presence of said porA amplification product indicates that said individual is or has been infected with *Neisseria gonorrhoeae*.

According to a particularly preferred form of this embodiment, real-time PCR detection is utilized at step (ii), by fluorescence resonance energy transfer (FRET) using an adjacent hybridization probe format. The preferred upstream oligonucleotide probe (NGpapP1; Table 1; SEQ ID NO:3) is labelled with a donor fluorophore, fluorescein, at the 3' terminus, and the preferred downstream oligonucleotide probe (NGpapP2; Table 1; SEQ ID NO:4) is labelled with, an acceptor fluorophore. LC-Red640, at the 5' terminus. Probe NGpapP2 (SEQ ID NO:4) is also phosphorylated at the 3' terminus.

It will be further appreciated that the present invention may be performed in conjunction with nucleic acid-based detection of other pathogenic organisms.

In this regard, the invention contemplates nucleic acid array detection of a porA nucleic acid of *Neisseria gonorrhoeae*, wherein one or more other nucleic acids of other pathogenic organisms may be detected.

A general discussion of this type of microarray approach to multi-pathogen detection is provided in Bryant et al., 2004, Lancet Infect. Dis, 4 100.

It will be appreciated that the nucleic acid array may comprise an oligonucleotide according to the second aspect, immobilized, coupled, impregnated or otherwise in communication with a substrate.

More generally, nucleic acid array technology has become well known in the art and examples of methods applicable to array technology are provided in Chapter 22 of CURRENT PROTOCOLS IN MOLECULAR, BIOLOGY Eds. Ausubel et al. (John Wiley & Sons NY USA 1995-2001).

In certain embodiments, at least one address of the plurality includes a nucleic acid capture probe that hybridizes specifically to a member of a nucleic acid library, e.g., the sense or anti-sense strand. In one preferred embodiment, a subset of addresses of the plurality of addresses has a nucleic acid capture probe for a nucleic acid library member. Each address of the subset can include a capture probe that hybridizes to a different region of a library member.

With respect to the present invention, a preferred array format comprises glass slides having an immobilized, ordered grid of a plurality of cDNA fragments.

The array can have a density of at least man 10, 50, 100, 200, 500, 1,000, 2,000, or 10,000 or more addresses/cm, and ranges therebetween. The substrate may be a two-dimensional substrate such as a glass slide, a wafer (e.g., silica or plastic), a mass spectroscopy plate, or a three-dimensional substrate such as a gel pad.

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT/US93/04145).

So that the present invention can be readily understood and put into practical effect, reference is made to the following son-limiting examples.

EXAMPLES

Materials & Methods

Patient Specimens

A total of 282 clinical samples (46 cervical swabs, 12 urethral swabs and 224 urine specimens) from patients presenting for sexual health screen were used in this study. Given the low incidence of *N. gonorrhoeae* infection in our local population, the samples were selected to provide a large proportion of Cobas positive specimens.

The patients comprised 178 females and 104 males and ranged in age from 13 to 70 years with a mean age of 26 years and a median age of 23 years. All 282 samples were tested by the NGpapLC assay and by a testing algorithm combining the Roche Cobas Amplicor assay and the cppB-LC assay. Using this algorithm, specimens, were initially tested by the Cobas Amplicor method. Any sample providing a positive *N. gonorrhoeae* result by the Cobas Amplicor assay was then tested by the cppB-LC assay for confirmation.

Roche Cobas Amplicor Assay

The urine and swab specimens were processed and tested on the Roche Cobas Amplicor System according to the manufacturer's instructions. Each specimen was simultaneously tested for *N. gonorrhoeae*, Chlamydia trachomatis and the presence of inhibiting substances. Result interpretation was performed using the criteria supplied by the manufacturer. Briefly, specimens providing as absorbance less than 0.2 were considered negative for *N. gonorrhoeae* whereas specimens providing an absorbance value of 0.2 or greater were considered positive.

LightCycler Assays (NGpapLC and cppB-LC)

A column extraction was used for both the NGpapLC and cppB-LC LightCycler assays. Nucleic acids were extracted from 0.2 ml of each specimen using the High Pure Viral Nucleic Acid kit (Roche Diagnostics, Australia), according to the manufacturer's instructions. Purified specimen DNA was eluted from the column in 50 µl of elation buffer (Roche Diagnostics, Australia). DNA extracts were stored at −20° C. until analysis.

The NGpapLC assay comprised of one primer pair, one pair of hybridization probes and targeted the *N. gonorrhoeae* porA pseudogene. Amplification was performed using primers papF and papR (Table 1; Invitrogen, Australia), which produced a 132 bp PCR product during the reaction. Realtime PCR detection was achieved by fluorescence resonance energy transfer (FRET) using an adjacent hybridization probe format. The upstream oligonucleotide probe (papP1; Table 1) was labelled with a donor fluorophore, fluorescein, at the 3' terminus, and the downstream oligonucleotide probe (papP2; Table 1) was labelled with an acceptor fluorophore, LC-Red640, at the 5' terminus (TIBMOLBIOL, Germany). Probe papP2 was also phosphorylated at the 3' terminus. The LightCycler FastStart DMA Master Hybridization Probes kit (Roche Diagnostics, Australia) was used as the basis for the reaction mixture, employing a 20 µl volume in each reaction capillary. Briefly, capillaries were loaded with 2 µl of kit Master reagent (10×; Roche Diagnostics, Australia, reagent 1), 4 mM of MgCl$_2$ (Roche Diagnostics, Australia, reagent 2), 0.4 µM of primer papF, 0.6 µM of primer papR, 0.2 µM of each hybridization probe and 5 µl of DNA extract. Each mix was made up to 20 µl using sterile PCR-grade water (Roche Diagnostics, Australia, reagent 3). Every test ran included a positive control and three no-target controls consisting of 15 µl of reaction mixture with 5 µl of extraction elution buffer. Amplification and detection was performed on the LightCycler (software version 5.32) using the following parameters: an initial denaturation step at 95° C. for 10 minutes followed by 55 cycles of denaturation at 95° C. for 10 seconds, primer and probe annealing at 55° C. for 10 seconds and extension at 72° C. for 20 seconds. The fluorescence response data were obtained during the annealing period and analysed with the channel settings F2/F1. Melting curve analysis was performed following PCR amplification. Briefly, the analysis was commenced at 40° C., and the temperature was raised to 95° C. at a rate of 0.2° C./s.

The cppB-LC assay was performed as previously described (Whiley et al., 2002, supra) and utilized similar conditions to those of the NGpapLC assay. Briefly, the LightCycler FastStart DNA Master Hybridisation Probes kit (Roche Diagnostics, Australia) was used as the basis of the reaction mix. Each reaction capillary comprised a total reaction volume of 20 µl, which included two primers (HO1 @ 0.2 µM and HO2 @ 0.4 µM) and two hybridisation probes (0.2 µM each) targeting the *N. gonorrhoeae* cppB gene (Whiley et al., 2002, supra).

Defection Limit

The detection limits of the NGpapLC and cppB-LC assays were determined and compared by testing dilations of a suspension of a *N. gonorrhoeae* culture (ATCC49226) at 5×10E4 colony forming units/ml (cfu/ml). Serial 10-fold dilutions of this suspension were extracted and tested by both assays using the conditions described above. The detection limit of each assay was determined as the lowest concentration returning a positive reaction.

Neisseria Panel

A panel of *Neisseria* species was tested by both the NGpapLC and cppB-LC assays. This panel included 63 non-gonococcal *Neisseria* isolates, which were tested to determine false-positive cross-reactions. The species comprised *N. meningitidis* (38), *N. subflava* (12), *N. sicca* (6), *N. elongata* (3), *N. mucosa* (1), *N. lactamica* (3) and *Branhamella catarrhalis* (6), which is closely related to the *Neisseria* genus. In addition, 84 *N. gonorrhoeae* isolates were tested to determine if the primer and probe sequence targets of each assay were conserved. Six *N. gonorrhoeae* isolates were included that had previously tested negative by the cppB-LC assay. These six isolates were provided by Royal Darwin Hospital, Northern Territory. The remaining *N. gonorrhoeae* isolates were selected from different geographical locations throughout the state of Queensland to ensure a broad cross section of isolates. Nucleic acids were extracted from cultures of each isolate using the High Pure Viral Nucleic Acid kit (Roche Diagnostics, Australia), according to the manufacturer's instructions. Approximately 0.5 µg of bacterial DNA was added to each reaction.

Non-*Neisseria* Panel—Common Human Pathogens and Normal Flora

An additional panel of common human pathogens and normal flora was also used to further determine the specificity of the NGpapLC assay; *Acinetobacter aranitratus* ATCC 19606, *Acinetobacter beautmanni* ACM 686, *Acinetobacter haemolyticus* ACM 620, *Acinetobacter johnsonii* ACM 621, *Acinetobacter junii* ACM 617, *Acinetobacter lwolfii* ACM 664, *Aeromonas hydrophilia* ATCC 35654, *Alcaligenes faecalis* ATCC 35655, *Bacillus amyloliquifaciens* ATCC 3642, *Bacillus brevis* ATCC 37, *Bacillus cereus* ATCC 11778, *Bacillus circulans* ATCC 61, *Bacillus coagulans* ATCC 264, *Bacillus firmus* ATCC 31, *Bacillus laterosporus* ATCC 295, *Bacillus licheniformis* ATCC 127559, *Bacillus macerans* ATCC 401, *Bacillus megaterium* ATCC 2640, *Bacillus mycoides* ATCC 28, *Bacillus polymyxa* ATCC 35, *Bacillus pumulis* ATCC 433, *Bacillus sphaericus* ATCC 4525, *Bacillus subtillus* ATCC 11774, *Bacillus thuringiensis* ATCC 453, *Bacteroides distasonis* ATCC 8503, *Bacteroides gingivalis* ATCC 33277, *Bacteroides vulgatus* ATCC 8482, *Bordetella bronchiseptica* ATCC 10580, *Bordetella parapertussis* ATCC 15237, *Burkholduria cepacia* ATCC 17765, *Campylobacter jejuni* ATCC 33291, *Candida albicans* ATCC 14053, *Candida krusei* (laboratory isolate), *Candida tropicalis* (laboratory isolate), *Citrobacter freundii* ATCC 8090, *Corynebacterium diptheriae* ATCC 13812, *Enterobacter aerogenes* ATCC 13048, *Enterobacter cloacae* (laboratory isolate), *Enterococcus durans* ATCC 6506, *Enterococcus faecalis* ATCC 29212, *Enterococcus faecium* ATCC 35667, *Erysipelothrix rhusiopathiae* ATCC 19414, *Esherichia coli* ATCC 35218, *Flavobacterium indologenes* (laboratory isolate), *Flavobacterium mutltivoram* ATCC 35656, *Haemophilis influenzae* ATCC 10211, *Klebsiella pneumoniae* ATCC 13883, *Listeria monocytogenes* ATCC 7646, *Micrococcus luteus* ATCC 4988, *Proteus mirabilus* ATCC 7002, *Proteus vulgaris* ATCC 6380, *Providencia stuartii* ATCC 35031, *Pseudomonas aeruginosa* ATCC 27853, *Pseudomonas vesicularis* (laboratory isolate), *Saccharomyces cerevisiae* ATCC 2366, *Salmonella typhimurium* ATCC 14028, *Serratia marcescens* (laboratory isolate), *Serratia oderifera* ATCC 33077, *Shigella flexneri* (laboratory isolate). *Shigella sonnei* ATCC 25931, *Staphylococcus simulans* ATCC 27851, *Staphylococcus aureus* (laboratory isolate), *Staphylococcus aureus* ATCC 33591, *Staphylococcus aureus* NCTC 6751, *Staphylococcus capitis* ATCC 27840, *Staphylococcus cohnii* ATCC 29974, *Staphylococcus epidermidis* (laboratory isolate), *Staphylococcus haemolyticus* ATCC 29970, *Staphylococcus hominus* ATCC 27844, *Staphylococcus intermedius* ATCC 29663, *Staphylococcus lugdenensis* (laboratory isolate), *Staphylococcus scuiri* (laboratory isolate), *Staphylococcus warneri* ATCC 27836, *Staphylococcus xylosus* ATCC 29971, *Stenotrophomonas maltophilia* (laboratory isolate), *Streptococcus agalactiae* ATCC 12386, *Streptococcus bovis* ATCC 9809, *Streptococcus equi* ATCC 9528, Streptococcus equisimilis ATCC 35666, Streptococcus (group B) ATCC 12386, Streptococcus (group F) ATCC 12392, Streptococcus (group G) ATCC 12394, Streptococcus mutans ATCC 35668, Streptococcus pneumoniae ATCC 27336, Streptococcus pyogenes ATCC19615, Streptococcus salivarius ATCC13419, Vibrio alginolyticus ATCC17749, Vibrio parahaemolyticus ATCC17802, Yarrowia lipolytica ATCC 9773 and Yersinia enterocolitica ATCC 23715. Genomic DNA was purified from cultures of these organisms and tested in the NGpapLC assay using the conditions described above.

Results

A total of 282 clinical samples were tested by the NGpapLC assay and by a testing algorithm combining the Roche Cobas Amplicor assay wife the cppB-LC assay. A summary of these results is provided in Table 2.

Overall 79 (28.0%) specimens were positive and 120 (42.6%) specimens were negative for N. gonorrhoeae DNA by all three PCR methods. An additional 81 (28.7%) specimens were positive by the Cobas Amplicor assay but negative by both the NGpapLC and cppB-LC assays. These were considered to be false-positive results obtained by the Cobas Amplicor. A further two (0.7%) specimens were positive by the Cobas Amplicor assay but gave discrepant results on the LightCycler assays; one specimen was positive by the cppB-LC assay with a cycle threshold value (Ct value) of 47 but negative by NGpapLC whereas the remaining specimen was positive by NGpapLC only, providing a Ct value of 41. These Ct values were the highest recorded Ct values for each test and are indicative of low N. gonorrhoeae DNA concentrations in each specimen. Upon repeat testing, neither specimen was consistently positive. This suggests that the concentration of DNA in both specimens was on the threshold of sensitivity of the respective test.

By testing dilutions of N. gonorrhoeae culture, ranging from 5×10E+4 to 5×10E−2 cfu/ml, the limit of sensitivity of the NGpapLC was determined to be 5 cfu/ml of N. gonorrhoeae in the specimen. The detection limit of the cppB-LC was determined to be 5×10E−1 cfu/ml. This suggests the cppB-LC has a 10-fold better detection limit than the NGpapLC assay.

To further determine the specificity of the NGpapLC assay, genomic DNA was purified and tested from cultures of a broad panel of organisms. These included Neisseria species as well as other common human pathogens and normal flora. All of the non-gonococcal species were negative when tested by the NGpapLC assay. In contrast, three N. meningitidis isolates tested positive by the cppB-LC assay. These three N. meningitidis isolates provided cycle threshold (Ct) values in the cppB-LC assay that were significantly greater than those provided by the positive N. gonorrhoeae isolates; the Ct values of the N. gonorrhoeae isolates were consistently lower than 16 whereas these three N. meningitidis isolates provided Ct values of 33 or greater. This suggests the cppB gene may be present at lower copy number in these N. meningitidis isolates.

Of the 84 N. gonorrhoeae isolates tested, seven were negative by the cppB-LC assay. Six of these seven negative isolates were the N. gonorrhoeae isolates obtained from the Northern Territory and had previously tested negative by the cppB-LC assay. Therefore only one additional cppB negative isolate was identified in the Queensland isolates. In contrast, all 84 N. gonorrhoeae isolates provided positive results when tested by the NGpapLC assay. This shows that the NGpapLC oligonucleotide targets were present in all isolates. In addition, fluorescent melting curve analysis by the NGpapLC assay showed no variation between N. gonorrhoeae isolates or any of the positive clinical specimens; all NGpapLC positive reactions provided melting temperatures of 65° C.

NGpapLC Compared to Bacterial Culture

A comparison with bacterial culture was performed on the local Queensland population and comprised of 557 specimens taken from patients attending sexual health clinics. This population was considered ideal for testing the specificity of the NGpapLC assay given the low incidence of N. gonorrhoeae in this population.

Compared to bacterial culture, the assay was 100% sensitive and 88.2% specific (Table 3).

However, this specificity calculation is based on the assumption that the two additional PCR positives are false-positive results. In contrast, we believe that these additional positive results are true positive results. This is because the results of the NgpapLC were supported by a second PCR assay targeting a separate N. gonorrhoeae gene. In addition, previous studies have shown that PCR has better clinical sensitivity than bacterial culture. Therefore, additional PCR positives would not be unexpected. Overall, the above results suggest the new NGpapLC assay is highly suitable for routine detection N. gonorrhoeae in clinical samples.

Tables 4-7 provide a breakdown of the Table 3 data into specimen types.

For both the urethral and cervical specimens the NGpapLC assay was 100% specific.

The results of the throat-swabs suggest the NGpapLC is also suitable for use on these specimen types, as does the more limited data on anal swabs.

Discussion

The problems associated with the specificity of the Cobas Amplicor N. gonorrhoeae assay and the requirements for a confirmatory assay are well documented. Unfortunately, the conventional gene targets used for confirmatory tests have also proved to have limitations. The results of this study suggest the NGpapLC assay is a suitable alternative to the cppB-LC for confirmation of Cobas Amplicor N. gonorrhoeae positive results. By targeting the N. gonorrhoeae porA pseudogene, the NGpapLC overcomes the limitations associated with the cppB gene and provides the potential for improved clinical sensitivity and specificity.

By testing dilutions of an ATCC strain of N. gonorrhoeae, the cppB-LC assay had a 10-fold better detection limit compared to our new NGpapLC assay. This presumably is because the cryptic plasmid is at a higher copy number than the N. gonorrhoeae porA pseudogene. Nevertheless, the difference in detection limits did not affect the clinical sensitivities of the assays. For the clinical specimens, the NGpapLC and cppB-LC assays gave good agreement for the detection of N. gonorrhoeae. Only two of the 282 specimens provided discrepant results, with each LightCycler assay detecting an additional positive over the other. Originally, it was considered that the additional cppB-LC positive result may have stemmed from the N. gonorrhoeae DNA load being below the detection limit of the NGpapLC assay. However, by using a more sensitive nested PCR assay we were still unable to detect the presence of the N. gonorrhoeae porA pseudogene in this specimen (data not shown). This suggests that this specimen was either a false-positive using our Roche Amplicor and cppB-LC testing algorithm or represents a N. gonorrhoeae strain lacking the porA pseudogene. Although, to date there have been no reports of N. gonorrhoeae strains lacking the porA pseudogene. It is further interesting to note that by using nested amplification we were able to detect the presence of the cppB gene in the specimen that was negative by the cppB-LC assay but positive by the NGpapLC test. This demonstrates that this cppB-LC negative result-did not occur because of the absence of the cppB gene in this presumptive *N. gonorrhoeae* strain (data not shown).

Overall, the results for the clinical specimens suggest the NGpapLC and cppB-LC assays have similar clinical sensitivities and specificities and that the cppB-LC assay may in fact be suitable for use on urine and genital swab specimens in our population. However, these results are in contrast with those of the bacterial panel, which highlighted the limitations of the cppB-LC assay. Most notably the cppB-LC assay failed to detect seven *N. gonorrhoeae* isolates. This shows that in our population there are *N. gonorrhoeae* strains lacking the cppB gene. More importantly, our testing algorithm is likely to produce false-negative results; specimens testing positive by the Cobas Amplicor could incorrectly be identified as false-positives by the cppB-LC assay. In this study, *N. gonorrhoeae* isolates were not randomly selected, therefore more testing is required to determine the overall cppB-LC false-negative rate. Other studies have suggested that the incidence of such isolates lacking the cppB gene is low in Australia (Leslie et al., 2003, Commun Dis Intell. 27 373-9).

Nevertheless, when using the cppB-LC assay the potential for false-negative results exists. In contrast, the NGpapLC method correctly identified all *N. gonorrhoeae* isolates tested in this study. This suggests the NGpapLC assay may not be susceptible to false-negative results arising from the absence of the porA pseudogene in our local *N. gonorrhoeae* strains. Hence, it should provide improved clinical sensitivity compared to the cppB-LC assay.

The NGpapLC assay also proved to be highly specific for *N. gonorrhoeae* DNA; all non-gonococcal species provided negative results when tested by the NGpapLC method. It should be noted mat we experienced difficulty obtaining *Neisseria* species and so our bacterial panel did not include all known *Neisseria* species and only contained a limited number of isolates for most species. Therefore, cross-reactions with oilier *Neisseria* species cannot, be ruled out on the basis of these results alone. However, the *Neisseria* porA gene is only reported to exist in *N. gonorrhoeae* and *N. meningitidis* (Feavers & Maiden 1998, supra % and therefore cross-reactions with *N. meningitidis* were considered to be more relevant. In this study, we tested 38 *N. meningitidis* isolates and found no cross-reactions. As a result, we axe confident of the specificity of this test when used on our local sample population.

The cppB-LC results for the bacterial panel provided a good example of the specificity problems associated with using the cppB target as positive results were obtained from three *N. meningitidis* cultures. Nevertheless, the presence of the cppB gene in local *N. meningitidis* isolates may not pose a major specificity problem if testing is restricted to urine and genital swab specimens. To date there have been no reports of *N. meningitidis* producing false-positive results in the Cobas Amplicor assay, and such isolates would be negative when initially screened by the Cobas Amplicor. On the other hand, the cppB gene has been found in isolates of other *Neisseria* species, including *N. cinerea*, which also cross-reacts with the Cobas Amplicor assay (Palmer et al., 2003, supra; Farrell, 1999, supra). Further, our study only examined a limited number of *Neisseria* species and strains, therefore, the possibility of cross-reactions wife other *Neisseria* species. In our population cannot be excluded.

The importance surrounding the specificity of a confirmatory assay for *N. gonorrhoeae* is also dependent on specimen site. One of the key limitations of the Cobas Amplicor is that its specificity significantly declines when used on extra-genital sites. In particular, throat swabs are a major problem as they can possess various *Neisseria* species and so offer greater potential for false-positive cross-reactions. A recent study (Leslie et al., 2003, supra) found feat confirmation rates of Cobas Amplicor *N. gonorrhoeae* positive results dropped from 86.2% fox penile and urethral swabs to 5.6% for oropharyngeal swabs. It should be noted that even when using the cppB-LC confirmatory assay, the number of true positives obtained from throat swabs are likely to be much lower than those obtained from genital specimens. This is because the presence of multiple *Neisseria* species in throat swabs increases the chance of both assays providing false-positive results; one species could cross-react with the screening assay while another species may cross-react with the confirmatory assay, thus producing a false-positive result from the algorithm. We believe that the specificity provided by our new NGpapLC confirmatory assay may provide improved detection of *N. gonorrhoeae* in extra-genital sites. Our aim is to extensively evaluate the use of the NGpapLC assay on multiple specimen types, including throat swabs.

The results of this study show the porA pseudogene is a suitable target for PCR detection of *N. gonorrhoeae*. It is worth highlighting that the porA gene was previously a popular target for the detection of *N. meningitidis* by PCR. However, it has since lost favour since it was discovered that insertion sequences may be incorporated into the porA gene of some *N. meningitidis* isolates giving false-negative results (van der Ende et al., 1999, Infect Immun. 67 2928-34; Newcombe et al., 1998, Mol Microbiol 30 453-4; Jelfs et al. 2000, Clin Diagn Lab. Immunol 7 390-5).

Such mutations can potentially block PCR amplification or probe hybridization and hence prevent detection of some *N. meningitidis* isolates. The fact that all *N. gonorrhoeae* isolates were detected in tins study suggests that insertion sequences may not be found in the *N. gonorrhoeae* porA pseudogene. However, given that the selection of our *N. gonorrhoeae* isolates was not random, it is possible that *N. gonorrhoeae* isolates containing insertion sequences were simply missed by the study. Alternatively, insertion sequences may have been present but did not affect the NGpapLC assay because of its small PCR product size (132 bp); such a small PCR product size may reduce the probability of sequences inserting between the PCR primer targets. We aim to further evaluate the NGpapLC assay against an extended panel of *N. gonorrhoeae* isolates.

Throughout the specification the aim has been to describe the preferred embodiments of the invention without limiting the invention to any one embodiment or specific collection of features. It will therefore be appreciated by those of skill, in the art that, in light, of the instant disclosure, various modifications and changes can be made in the particular embodiments exemplified without departing from the scope of the present invention.

All patent and scientific literature, algorithms and computer programs referred to in this specification are incorporated herein be reference in their entirety.

This application claims priority to AU 2004901890 filed Apr. 8, 2004, the entirety of which is hereby incorporated by reference.

TABLE 1

NGpapLC primers and probes targeting the N. gonorrhoeae porA pseudogene
(SEQ ID NOS 1-4, respectively in order of appearance)

| Designation | Sequence (5' to 3') | Position |
|---|---|---|
| papF: | CGGTTTCCGTGCGTTACGA (SEQ ID NO: 1) | 681-699[a] |
| papR: | CTGGTTTCATCTGATTACTTTCCA (SEQ ID NO: 2) | 812-789[a] |
| papP1: | CATTCAATTTGTTCCGAGTCAAAACAGC (SEQ ID NO: 3)-fluorescein | 730-757[a] |
| papP2: | LCred640-AGTCCGCCTATACGCCTGCTACTTTCAC (SEQ ID NO: 4)-Phosphate | 759-786[a] |

[a] Genbank accession number AJ223448

TABLE 2

An improved confirmatory *Neisseria gonorrhoeae* real-time PCR assay targeting the porA pseudogene.

| N = 282 | Cobas Amplicor & cppB-LC testing algoritm positive | Cobas Amplicor & cppB-LC testing algoritm negative |
|---|---|---|
| NGpapLC positive | 79 | 1 |
| NGpapLC negative | 1 | 201* |

*81 of these specimens were positive by the Cobas Amplicor assay but negative by the cppB-LC assay.

TABLE 3

All specimen types: PCR v Culture

| N = 557 | Culture positive | Culture negative |
|---|---|---|
| NGpapLC positive | 15 | 2* |
| NGpapLC negative | 0 | 540 |

*Currently, there is no assay available that could reliably be used for discrepant analysis on these specimens. However, these specimens were also positive by the cppB-LC (which can also cross-react with other *Neisseria* species). Further, these specimens provided comparable Ct values in both the NGpapLC and cppB-LC assays. This suggests that the bacterial DNA detected by these assays were at approximately the same concentration. Overall, these results suggest that these are true *N. gonorrhoeae* positive specimens.

TABLE 4

Cervical swabs: PCR v Culture

| N = 216 | Culture positive | Culture negative |
|---|---|---|
| NGpapLC positive | 1 | 0 |
| NGpapLC negative | 0 | 215 |

TABLE 5

Urethral swabs: PCR v Culture

| N = 184 | Culture positive | Culture negative |
|---|---|---|
| NGpapLC positive | 9 | 0 |
| NGpapLC negative | 0 | 175 |

TABLE 6

Throat swabs: PCR v Culture

| N = 133 | Culture positive | Culture negative |
|---|---|---|
| NGpapLC positive | 1 | 1* |
| NGpapLC negative | 0 | 131 |

TABLE 7

Anal swabs: PCR v Culture

| N = 24 | Culture positive | Culture negative |
|---|---|---|
| NGpapLC positive | 4 | 1* |
| NGpapLC negative | 0 | 19 |

The invention claimed is:

1. A method of determining whether an individual is infected with *Neisseria gonorrhoeae*, said method comprising the step of subjecting a biological sample obtained from said individual to nucleic acid sequence amplification using one or more PCR primers selected from the group consisting of SEQ ID NO:1 and SEQ ID NO:2 under conditions which facilitate amplification of an isolated porA nucleic acid of *Neisseria gonorrhoeae*, if present in said biological sample, to produce an amplification product comprising a nucleic acid sequence comprising residues 681-812 of SEQ ID NO:10, wherein the presence of said amplification product indicates that said individual is infected with *Neisseria gonorrhoeae*.

2. The method of claim 1, wherein said method includes the step of distinguishing said isolated porA nucleic acid of *Neisseria gonorrhoeae* from a porA nucleic of *Neisseria meningitidis* present in said biological sample.

3. The method of claim 1, wherein said isolated porA nucleic acid of *Neisseria gonorrhoeae* is distinguished from another *Neisseria* species other than *Neisseria meningitidis*.

4. The method of claim 1, wherein the nucleic acid sequence amplification is performed under conditions which facilitate amplification of said isolated porA nucleic acid of *Neisseria gonorrhoeae* to a detectable level but which do not facilitate amplification of a porA nucleic acid of *N. meningitidis*.

5. The method of claim 1, further comprising the step of using one or more oligonucleotide probes for detecting said amplification product by probe hybridization, wherein the probe comprises a nucleotide sequence selected from the group consisting of SEQ ID NO:3 and SEQ ID NO:4.

6. The method of claim 5, wherein detection of said amplification product is performed using fluorescence resonance energy transfer (FRET).

7. The method of claim 1, including the step of subjecting the amplification product to nucleotide sequencing.

8. A method of determining whether a human individual is infected with *Neisseria gonorrhoeae*, said method comprising the steps of:
  (i) subjecting a biological sample obtained from said human individual to nucleic acid amplification using primers comprising a nucleotide sequence selected from the group consisting of SEQ ID NO:1 and SEQ ID NO:2, to produce a porA *Neisseria gonorrhoeae* amplification product from a *Neisseria gonorrhoeae* porA nucleic aid if present in said biological sample; and
  (ii) detecting said amplification product, if present, by probe hybridization and fluorescence resonance energy transfer (FRET) using oligonucleotides comprising the nucleotide sequence of SEQ ID NO:3 having a donor fluorophore; and SEQ ID NO:4 having an acceptor fluorophore, whereby the presence of said porA amplification product indicates that said individual is infected with *Neisseria gonorrhoeae*.

9. A method of determining whether an individual is infected with *Neisseria gonorrhoeae*, said method comprising the step of detecting an isolated porA nucleic acid of *Neisseria gonorrhoeae*, if present in a biological sample obtained from said individual, wherein the presence of said isolated porA nucleic acid indicates that said individual is infected with *Neisseria gonorrhoeae*, wherein said isolated porA nucleic acid is an amplification product obtainable by nucleic acid sequence amplification using PCR primers comprising the nucleotide sequence of SEQ ID NO:1 and SEQ ID NO:2.

10. The method of claim 9, further including the step of using one or more oligonucleotide probes for detecting said amplification product by probe hybridization, wherein the probe comprises a nucleotide sequence selected from the group consisting of SEQ ID NO:3 and SEQ ID NO:4.

11. The method of claim 10, wherein detection of said amplification product is performed using fluorescence resonance energy transfer (FRET).

12. The method of claim 9, including the step of subjecting the amplification product to nucleotide sequencing.

* * * * *

SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 1
cggtttccgt gcgttacga              19

```
<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctggtttcat ctgattactt tcca                                              24

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cattcaattt gttccgagtc aaaacagc                                          28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agtccgccta tacgcctgct actttcac                                          28

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgctactttc acgctggaaa gta                                               23

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gaaagtaatc agatgaaacc agttc                                             25

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aggggcatga tgctttcttt ttgttc                                            26
```

```
<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cttgctcggc agagcgagtg ata                                               23

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gccgagcaag aacaaaaaga aagca                                             25

<210> SEQ ID NO 10
<211> LENGTH: 680
<212> TYPE: DNA
<213> ORGANISM: Neisseria gonorrhoeae

<400> SEQUENCE: 10
aaggtctgta tttaaatcat gttgcgggaa agcaacattt tcaaaaaagt taatttattg       60
ttttatattg aaatattatt tttcaaaata aaaatcccaa aatttacccg aaatttgttc      120
cgaaaaatgg ttttttttcg ggggggtaa ttggagactg attgggtgtt tgcccgatgt       180
ttttagcaaa tttacaaaag gaagccgata tgcgaaaaaa acttaccgcc ctcgtattgt      240
ccgcactgcc gtttgcggca gttgccgatg tcggcctgta cggcgaagtc aaagctggtg      300
tggaaggcag gaacatccgg ctgcagttga ccgagccacc ctcagaaggt caaacgggca      360
atacagttac taaggccaaa agccgcatca ggacgaaagt cagtgatttc ggctcgttta      420
tcggctttaa gggggtgggg atttgggcgg cgggctgaag gctgtttggc agctcgagca      480
agacgtatcc gttgccggcg gcggcgcgac ccgttgggt aacagggaat cctttatcgg       540
cttggcaggc gaattcggca cggcgctcgc cggtcgcgtt gcgaatccgt ttggcgatgc      600
cagcaaagcc attgatcctt gggacagcaa taataatgtg gcttcgcaat tgggtatttt      660
caaacgccac gacggtatgc                                                  680

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tggaaagtaa tcagatgaaa ccag                                              24

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 12
tgctttcttt ttgttcttgc tcggc                                            25

<210> SEQ ID NO 13
<211> LENGTH: 292
<212> TYPE: DNA
<213> ORGANISM: Neisseria gonorrhoeae

<400> SEQUENCE: 13
cggtttccgt gcgttacgat tcccccggat tttccggttt cagcggcagc attcaatttg       60
ttccgagtca aaacagcaag tccgcctata cgcctgctac tttcacgctg gaaagtaatc      120
agatgaaacc agttccggct gttgtcggca agccggggtc ggatgtgtat tatgccggtc      180
tgaattacaa aaatggcggc tttttcggaa attatgccct taaatatgcg aaacacgcca      240
atgaggggca tgatgctttc ttttttgttct tgctcggcag agcgagtgat ac             292

<210> SEQ ID NO 14
<211> LENGTH: 378
<212> TYPE: DNA
<213> ORGANISM: Neisseria gonorrhoeae

<400> SEQUENCE: 14
cgatccattg aaaaaccatc aggtacaccg cctgacgggc ggctatgagg aagcggcttg       60
aatctcgcct tggcggctca gttggatttg tctgaaaatg ccgacaaaac caaaaacagt      120
acgaccgaaa ttgccgccac tgcttcctac cgcttcggta atacagtccc gcgcatcagc      180
tatgcccatg gtttcgactt tgtcgaacgc agtcagaaac gcgaacatac cagctatgat      240
caaatcatcg ccggtgtcga ttacgatttt tccaagcgca cttccgccat catgtctgcc      300
gcttggctga aacgaaatac cggcatcggc aactacactc aaattaatgc cgcctccgtt      360
ggtctgcgcc acaaattc                                                    378
```